United States Patent
Park et al.

(10) Patent No.: US 12,064,359 B2
(45) Date of Patent: *Aug. 20, 2024

(54) THUMB-BASED HAND MOTION CONTROL SYSTEM FOR MYOELECTRIC HAND AND CONTROL METHOD THEREOF

(71) Applicant: KOREA LABOR WELFARE CORPORATION CO., LTD., Ulsan (KR)

(72) Inventors: Se Hoon Park, Bucheon-si (KR); Jong Moon Choi, Seoul (KR); Sung Yoon Jung, Incheon (KR); Hui Tae Lee, Incheon (KR); Seung Gi Kim, Incheon (KR)

(73) Assignee: KOREA LABOR WELFARE CORPORATION CO., LTD., Ulsan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/425,925

(22) PCT Filed: Jun. 12, 2019

(86) PCT No.: PCT/KR2019/007038
§ 371 (c)(1),
(2) Date: Jul. 26, 2021

(87) PCT Pub. No.: WO2020/196988
PCT Pub. Date: Oct. 1, 2020

(65) Prior Publication Data
US 2024/0050245 A1    Feb. 15, 2024

(30) Foreign Application Priority Data
Mar. 28, 2019    (KR) .................. 10-2019-0036077

(51) Int. Cl.
*A61F 2/54* (2006.01)
*A61F 2/58* (2006.01)
(Continued)

(52) U.S. Cl.
CPC .............. *A61F 2/586* (2013.01); *A61F 2/583* (2013.01); *A61F 2/72* (2013.01); *A61F 5/013* (2013.01);
(Continued)

(58) Field of Classification Search
None
See application file for complete search history.

(56) References Cited

U.S. PATENT DOCUMENTS 6,896,704 B1    5/2005   Higuchi et al.
10,583,017 B2   3/2020   Donati et al.
(Continued)

FOREIGN PATENT DOCUMENTS

| KR | 10-2007-0080319 A | 8/2007 |
| KR | 10-2015-0106892 A | 9/2015 |
| KR | 101618706 B1 | 5/2016 |
| KR | 10-2012-0040431 A | 4/2021 |

OTHER PUBLICATIONS

KR Office Action dated Oct. 16, 2020 as received in Application No. 10-2019-0036077.
(Continued)

*Primary Examiner* — David H Willse
(74) *Attorney, Agent, or Firm* — Maschoff Brennan (57) ABSTRACT

The present invention relates to a hand motion control system and a control method thereof, and more specifically, to a hand motion control system for a myoelectric hand, and to a control method thereof. The system enables not only grasping motions for grasping an object, but also the expression of hand gestures expressing emotions or intent, based on a limited myoelectric signal transmitted via two myo- (Continued)

electric sensors provided on the myoelectric hand. Furthermore, the system enables a wide variety of hand postures and grasp types that are determined by the position of a thumb, which can be changed by a user, thus easily expanding the range of applications of the myoelectric hand.

12 Claims, 3 Drawing Sheets

(51) Int. Cl.
    *A61F 2/72*     (2006.01)
    *A61F 5/01*     (2006.01)
    *A61F 2/70*     (2006.01)
    *A61F 2/76*     (2006.01)

(52) U.S. Cl.
    CPC .............. *A61F 2002/587* (2013.01); *A61F 2002/704* (2013.01); *A61F 2002/7625* (2013.01); *A61F 2005/0155* (2013.01)

(56) References Cited

U.S. PATENT DOCUMENTS

| | | |
|---|---|---|
| 2008/0215162 A1* | 9/2008 | Farnsworth ............... A61F 2/68 600/587 |
| 2012/0123558 A1 | 5/2012 | Gill |
| 2013/0053984 A1 | 2/2013 | Hunter et al. |
| 2015/0351935 A1* | 12/2015 | Donati .................... A61F 2/586 623/24 |
| 2016/0051382 A1 | 2/2016 | Goldfarb et al. |
| 2016/0051383 A1 | 2/2016 | Goldfarb et al. |
| 2018/0064563 A1 | 3/2018 | Gill |
| 2018/0071115 A1 | 3/2018 | Lipsey et al. |

OTHER PUBLICATIONS

KR Decision to Grant Dated Apr. 20, 2021 as received in Application No. 10-2019-0036077.

European Search Report dated Nov. 11, 2022 as received in application No. 19921053.5.

\* cited by examiner

THUMB-BASED HAND MOTION CONTROL SYSTEM FOR MYOELECTRIC HAND AND CONTROL METHOD THEREOF

TECHNICAL FIELD

The present invention relates to a hand motion control system and a method of controlling the same, and more particularly to a thumb-based hand motion control system of a myoelectric hand that is capable of performing a hand motion indicating emotion or intention expression as well as a grasping motion for holding an object according to restrictive electromyography signals transmitted from two electromyography sensors provided at the myoelectric hand and that is capable of diversifying hand motions and grips depending on the position of a thumb that can be changed by a user, whereby a utilization range of the myoelectric hand is simply extended, and a method of controlling the same.

BACKGROUND ART

In recent years, research and development of various kinds of medical equipment or rehabilitation assistance apparatuses have been conducted in order to solve daily inconvenience that many handicapped people suffer from, thus improving quality of life.

In particular, a myoelectric hand for upper extremity amputees is a typical rehabilitation assistance apparatus that moves an artificial hand using an electromyography signal, which is an electric signal output from the muscle of an arm, to grasp an object, whereby handicapped people engage in independent social activities and daily lives.

For the myoelectric hand, five-finger type products configured not only to stably hold various kinds of objects but also to express various intentions, such as "OK" and "V", using hand motions have increasingly come onto the market in recent years.

However, such a five-finger type myoelectric hand has not completely substituted for a conventional three-finger type myoelectric hand even up to now, i.e. 12 years after the five-finger type myoelectric hand was first developed, and has many disadvantages in terms of durability, price, maintenance expenses, and convenience.

In particular, it is difficult to change hand motions in implementing various hand motions using the five-finger type myoelectric hand, and therefore many problems are caused in utilizing all advantages in that it is possible to implement 10 to 30 different hand motions, compared to conventional hand motions implemented to perform a simple grasping function.

That is, the conventional five-finger type myoelectric hand is capable of implementing various hand motions and grasping motions. In order to change motions, however, an additional control signal other than a control signal constituted by only electromyography signals that a user can apply to the remaining muscle in order to perform a grasping motion is necessary, or an additional device, such as an application (APP) or dongle (wireless chip), is necessary. As a result, complexity in manipulation greatly increases.

Addition of devices or increase in complexity of manipulation deteriorates durability and convenience in use of the myoelectric hand. In addition, manufacturing cost and maintenance expenses increase. As a result, wide popularization of the five-finger type myoelectric hand is impeded.

DISCLOSURE

Technical Problem

It is an object of the present invention to provide a thumb-based hand motion control system of a myoelectric hand that is capable of performing a hand motion indicating emotion or intention expression as well as a grasping motion for holding an object according to restrictive electromyography signals transmitted from two electromyography sensors provided at the myoelectric hand and that is capable of diversifying hand motions and grips depending on the position of a thumb that can be changed by a user, whereby a utilization range of the myoelectric hand is simply extended, and a method of controlling the same.

Technical Solution

In order to accomplish the above object, a thumb-based hand motion control system of a myoelectric hand includes: a motion mode switching unit configured to switch a motion that is performed by the myoelectric hand between a hand motion mode for intention and emotion expression and a grasping motion mode for holding an object to change a controller to be enabled; a thumb sensor configured to determine whether a thumb provided at the myoelectric hand is located at a horizontal position or a vertical position; a hand motion controller configured to, when a detail mode matched with each of the horizontal position and the vertical position depending on the position of the thumb is selected in the hand motion mode enabled by the motion mode switching unit, receive an electromyography signal transmitted from at least one of first and second electromyography sensors attached to a human body, to enable a control signal for driving the myoelectric hand in order to implement a hand motion matched with each detail mode, and to transmit the control signal to a driving unit of the myoelectric hand; and a grasping motion controller configured to, when a detail mode matched with each of the horizontal position and the vertical position depending on the position of the thumb is selected in the grasping motion mode enabled by the motion mode switching unit, receive an electromyography signal transmitted from at least one of the first and second electromyography sensors, to enable a control signal for driving the myoelectric hand in order to implement a grasping motion matched with each detail mode, and to transmit the control signal to the driving unit of the myoelectric hand.

The motion mode switching unit may switch the controller to be enabled between the hand motion controller and the grasping motion controller whenever a simultaneous enabling signal, in which values of HIGH are applied from both the first and second electromyography sensors, is input.

The hand motion controller may include:
a hand motion setting unit configured to store a control signal matched with a driving signal for manipulating the driving unit of the myoelectric hand so as to unbend or bend fingers according to an enabling signal constituted by the electromyography signal transmitted from the first or second electromyography sensor in each detail mode of the hand motion mode; a thumb sensing unit configured to select and enable a detail mode matched with position information of the thumb transmitted from the thumb sensor in the state in which the hand motion mode is enabled; and a hand motion execution unit configured to derive a preset control signal according to the enabling signal transmitted from the first or second electromyography sensor in the state in which the detail mode selected by the thumb sensing unit is enabled and to transmit the control signal to the driving unit.

The hand motion setting unit may be configured to generate and store a control signal in which each enabling signal is matched with a driving signal for bending or unbending joints of the fingers in order to show a first hand motion to be performed in a first enabling signal state in which a value of HIGH is input from the first electromyography sensor and a value of LOW is input from the second electromyography sensor and a second hand motion to be performed in a second enabling signal state in which a value of LOW is input from the first electromyography sensor and a value of HIGH is input from the second electromyography sensor in a detail mode of the hand motion mode in which the thumb is located at the vertical position.

The hand motion setting unit may be configured to generate and store a control signal in which each enabling signal is matched with a driving signal for bending or unbending joints of the fingers in order to show a third hand motion to be performed in a first enabling signal state in which a value of HIGH is input from the first electromyography sensor and a value of LOW is input from the second electromyography sensor and a fourth hand motion to be performed in a second enabling signal state in which a value of LOW is input from the first electromyography sensor and a value of HIGH is input from the second electromyography sensor in a detail mode of the hand motion mode in which the thumb is located at the horizontal position.

The grasping motion controller may include:
a grasping motion setting unit configured to store a control signal matched with a driving signal for manipulating the driving unit of the myoelectric hand so as to grasp an object while unbending or bending fingers according to an enabling signal constituted by the electromyography signal transmitted from the first or second electromyography sensor in each detail mode of the grasping motion mode; a thumb sensing unit configured to select and enable a detail mode matched with position information of the thumb transmitted from the thumb sensor in the state in which the grasping motion mode is enabled; and a grasping motion execution unit configured to derive a preset control signal according to an enabling signal transmitted from the first or second electromyography sensor in the state in which the detail mode selected by the thumb sensing unit is enabled and to transmit the control signal to the driving unit.

The grasping motion setting unit may be configured:
to generate and store a control signal in which each enabling signal is matched with a driving signal for bending or unbending the joints of the fingers in order to show a first grasping motion to be performed in a first enabling signal state in which a value of HIGH is input from the first electromyography sensor and a value of LOW is input from the second electromyography sensor and a second grasping motion to be performed in a second enabling signal state in which a value of LOW is input from the first electromyography sensor and a value of HIGH is input from the second electromyography sensor in a detail mode of the grasping motion mode in which the thumb is located at the vertical position; and to generate and store a control signal in which each enabling signal is matched with a driving signal for bending or unbending the joints of the fingers in order to show a third grasping motion to be performed in the first enabling signal state and a fourth grasping motion to be performed in the second enabling signal state in a detail mode of the grasping motion mode in which the thumb is located at the horizontal position.

In addition, a thumb-based hand motion control method of a myoelectric hand according to the present invention includes:
a thumb-based motion setting step of classifying motion modes to be implemented by the myoelectric hand into a hand motion mode and a grasping motion mode and setting and storing, for each motion mode, a control signal for forming the shape of fingers or a grip to be implemented in each motion mode; a motion mode switching step of, when HIGH signals are input from two electromyography sensors provided at the myoelectric hand, switching a motion mode to be enabled between the hand motion mode and the grasping motion mode; a thumb position sensing step of acquiring the position of a thumb manipulated by a user based on position information transmitted from a thumb sensor; a detail mode selection step of determining whether the position of the thumb is a horizontal position or a vertical position and enabling a detail mode set in each motion mode; a control signal enabling step of deriving a control signal for performing a hand motion or a grasping motion set in each detail mode according to electromyography signals transmitted from the two electromyography sensors; and a motion implementing step of, upon receiving the enabled control signal, the myoelectric hand performing the set hand motion or grasping motion while bending or unbending joints of the fingers.

The thumb-based motion setting step may include:
a motion mode setting process of setting motions to be implemented by the myoelectric hand so as to be classified into a hand motion mode for showing shapes of fingers used for emotion expression or intention expression and a grasping motion mode for forming various grips to hold an object; a detail mode setting process of storing the shapes of fingers or grips to be implemented in each motion mode in a state of being matched with the vertical position and the horizontal position based on position information of the thumb; and a control signal matching process of storing a control signal for driving the myoelectric hand such that joints of the fingers of the myoelectric hand are bent or unbent in order to implement the shapes of fingers and the grips matched respectively with the vertical position and the horizontal position of the thumb in the detail mode in a state of being matched with each shape of fingers and each grip.

Advantageous Effects

The present invention has effects in that it is possible to perform a hand motion indicating emotion or intention expression as well as a grasping motion for holding an object according to restrictive electromyography signals transmitted from two electromyography sensors provided at a myoelectric hand and in that it is possible to diversify hand motions and grips depending on the position of a thumb that can be changed by a user.

BEST MODE

Hereinafter, concrete embodiments of the present invention will be described in detail with reference to the accompanying drawings.

Figure 1:
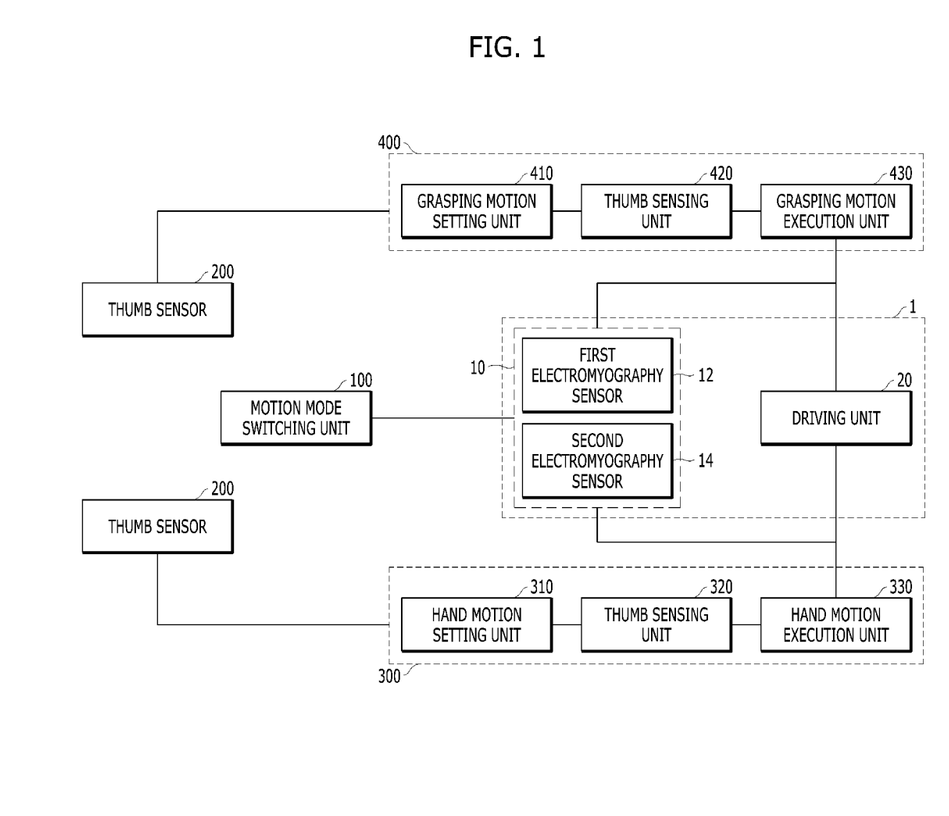
FIG. 1 is a block diagram of a thumb-based hand motion control system of a myoelectric hand according to the present invention.
Figure 2:
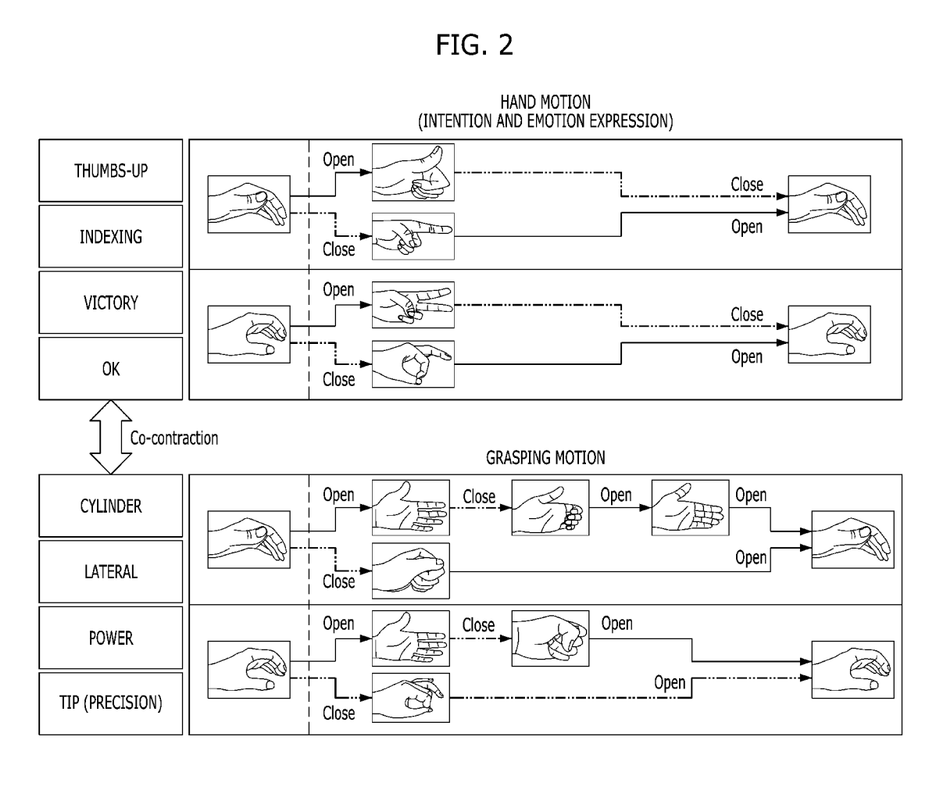
FIG. 2 is an illustrative picture showing hand motions and grasping motions based on the position of a thumb and the state of an electromyographic signal in accordance with the present invention.

FIG. 1 is a block diagram of a thumb-based hand motion control system of a myoelectric hand according to the present invention, and FIG. 2 is an illustrative picture showing hand motions and grasping motions based on the position of a thumb and the state of an electromyographic signal in accordance with the present invention.

Referring to FIGS. 1 and 2, the thumb-based hand motion control system of the myoelectric hand according to the present invention includes a motion mode switching unit 100 configured to switch a motion that is performed by the myoelectric hand between a hand motion mode for intention and emotion expression and a grasping motion mode for holding an object to change a motion controller to be enabled when electromyography signals are applied together from two electromyography sensors provided at the myoelectric hand, a thumb sensor 200 configured to, when a user manually rotates a thumb provided at the myoelectric hand, determine whether the rotated thumb is located at a horizontal position or a vertical position, a hand motion controller 300 configured to, when a detail mode matched with each of the horizontal position and the vertical position depending on the position of the thumb is selected in the hand motion mode enabled by the motion mode switching unit, receive an electromyography signal transmitted from one of the electromyography sensors, to enable a control signal for driving the myoelectric hand in order to implement a hand motion matched with each detail mode, and to transmit the control signal to a driving unit of the myoelectric hand, and a grasping motion controller 400 configured to, when a detail mode matched with each of the horizontal position and the vertical position depending on the position of the thumb is selected in the grasping motion mode enabled by the motion mode switching unit, receive an electromyography signal transmitted from one of the electromyography sensors, to enable a control signal for driving the myoelectric hand in order to implement a grasping motion matched with each detail mode, and to transmit the control signal to the driving unit of the myoelectric hand, whereby it is possible to implement both the hand motion and the grasping motion using the same electromyography signals.

That is, in the present invention, in not only grasping an object but also performing a simple hand motion indicating intention expression or emotion expression of the user using a five-finger type articulated myoelectric hand 1, it is possible to implement both motions using only a electromyography signal conventionally used to control a grasping motion without provision of an additional device, such as an application (APP) or dongle capable of generating a new driving signal.

Consequently, signals applied by the user who wears the myoelectric hand in order to implement the hand motion for intention expression or emotion expression in the present invention are merely electromyography signals that can be acquired by the two electromyography sensors conventionally attached to the human body in order to perform an object grasping motion, whereby it is possible to more conveniently express a simple hand motion without learning a new complicated manipulation method.

In order to implement both the grasping motion and the hand motion using restrictive electromyography signals transmitted from the two electromyography sensors, the myoelectric hand 1 includes two electromyography sensors 10 attached to the skin of the user to acquire electromyography signals and a driving unit 20 driven according to the electromyography signals acquired by the electromyography sensors to bend or unbend joints of fingers.

Combinations of electromyography signals generated by the two electromyography sensors 12 and 14 may include the case in which both the two electromyography sensors sense enabling signals and the case in which only one of the two electromyography sensors senses an enabling signal. In the present invention, it is possible to grasp an object and to perform a simple hand motion using only such three signals.

That is, as shown in Table 1 below, signals generated by the two electromyography sensors 12 and 14 attached to the human body constitute a simultaneous enabling signal (shown as a co-contraction signal in FIG. 2), in which both a first electromyography signal transmitted from the first electromyography sensor 12 and a second electromyography signal transmitted from the second electromyography sensor 14 have values of HIGH, a first enabling signal (shown as an open signal in FIG. 2), in which the first electromyography signal has a value of HIGH and the second electromyography signal has a value of LOW, and a second enabling signal (shown as a close signal in FIG. 2), in which the first electromyography signal has a value of LOW and the second electromyography signal has a value of HIGH. At this time, when a value of HIGH is applied from each electromyography sensor, this refers to an enabling signal indicating that the electromyography sensor is enabled.

TABLE 1

| | Simultaneous enabling signal (co-contraction) | First enabling signal | Second enabling signal |
|---|---|---|---|
| First electromyography signal | HIGH | HIGH | LOW |
| Second electromyography signal | HIGH | LOW | HIGH |

Among the three signals, the simultaneous enabling signal, which is a switching signal capable of changing a motion mode between the hand motion mode and the grasping motion mode, is configured to be used by the motion mode switching unit 100, and the first enabling signal and the second enabling signal, which are control signals for performing the hand motion and the grasping motion preset in the hand motion mode and the grasping motion mode, are configured to be used by the hand motion controller 300 and the grasping motion controller 400, respectively. Consequently, the motion mode switching unit 100, which switches a motion to be performed using the myoelectric hand between the hand motion mode and the grasping motion mode, is configured to switch the controller to be enabled between the hand motion controller 300 and the grasping motion controller 400 whenever the simultaneous enabling signal, in which values of HIGH are applied from both electromyography sensors, is input. That is, when values of HIGH are input from both the first electromyography sensor 12 and the second electromyography sensor 14 in the current hand motion mode (shown as a co-contraction signal in FIG. 2), the motion mode switching unit 100 disables the hand motion mode, which is currently enabled, and enables the grasping motion mode, whereby the grasping motion controller 400 applies a control signal for bending or unbending fingers to the driving unit 20 of the myoelectric hand.

In addition, when values of HIGH are input from both the first electromyography sensor 12 and the second electromyography sensor 14 in the grasping motion mode (shown as a co-contraction signal in FIG. 2), the motion mode switching unit disables the grasping motion mode, which is currently enabled, and enables the hand motion mode, whereby the hand motion controller applies a control signal for bending or unbending fingers to the driving unit of the myoelectric hand.

Since a controller that is enabled and outputs a control signal is changed by the motion mode switching unit 100, as described above, it is possible to perform the grasping motion and the hand motion using the same electromyography signal transmitted from any one electromyography sensor without addition of a separate additional device.

In addition, the thumb sensor 200, which determines whether the thumb provided at the myoelectric hand is located at the horizontal position or the vertical position, is configured to sense the position of the thumb in order to set a detail mode of the hand motion that can be implemented in the hand motion mode and a detail mode of the grasping motion that can be implemented in the grasping motion mode.

At this time, the position of the thumb may be changed by the user manually rotating the thumb. In this embodiment, the case in which the rotated thumb is located so as to be parallel to other fingers is referred to as a horizontal position, and the case in which the rotated thumb is located so as to be perpendicular to other fingers is referred to as a vertical position. However, the present invention is not limited thereto. The position of the thumb may be variously set.

In addition, the position of the thumb may be configured to be changed according to an automated control signal. In this case, however, a new type of control signal for rotating the thumb must be generated. In the present invention, in which the hand motion is performed without addition of a means capable of generating signals other than electromyography signals that can be received from the two electromyography sensors, it is preferable to manually rotate the thumb in order to change the position of the thumb.

In addition, the hand motion controller 300 includes a hand motion setting unit 310 configured to store a control signal matched with a driving signal for manipulating the driving unit of the myoelectric hand so as to unbend or bend fingers according to an enabling signal constituted by an electromyography signal transmitted from the first or second electromyography sensor in each detail mode of the hand motion mode, a thumb sensing unit 320 configured to select and enable a detail mode matched with position information of the thumb transmitted from the thumb sensor in the state in which the hand motion mode is enabled, and a hand motion execution unit 330 configured to derive a preset control signal according to an enabling signal transmitted from the first or second electromyography sensor in the state in which the detail mode selected by the thumb sensing unit is enabled and to transmit the control signal to the driving unit.

At this time, the hand motion setting unit 310 is configured to store a driving signal for manipulating the driving unit of the myoelectric hand so as to unbend or bend the fingers in order to perform a hand motion to be shown in each detail mode of the hand motion mode in a state of being matched with an enabling signal transmitted from the first or second electromyography sensor.

To this end, the hand motion setting unit 310 is configured to generate and store a control signal in which each enabling signal is matched with a driving signal for bending or unbending the joints of the fingers in order to show a first hand motion to be performed in a first enabling signal state in which a value of HIGH is input from the first electromyography sensor and a value of LOW is input from the second electromyography sensor and a second hand motion to be performed in a second enabling signal state in which a value of LOW is input from the first electromyography sensor and a value of HIGH is input from the second electromyography sensor in a detail mode of the hand motion mode in which the thumb is located at the vertical position.

In addition, the hand motion setting unit 310 is also configured to generate and store a control signal in which each enabling signal is matched with a driving signal for bending or unbending the joints of the fingers in order to show a third hand motion to be performed in the first enabling signal state and a fourth hand motion to be performed in the second enabling signal state in a detail mode of the hand motion mode in which the thumb is located at the horizontal position.

In this embodiment, as shown in FIG. 2, in the detail mode in which the thumb is located at the vertical position, a "thumbs-up" hand motion is set in the first enabling signal state (shown as an open signal in FIG. 2), and an "indexing" hand motion indicating an object or a direction is set in the second enabling signal state (shown as a close signal in FIG. 2).

Also, in the detail mode in which the thumb is located at the horizontal position, a "V"-shape hand motion indicating "victory" is set in the first enabling signal state (shown as an open signal in FIG. 2), and a hand motion indicating "OK" is set in the second enabling signal state (shown as a close signal in FIG. 2).

The thumb sensing unit 320 is configured to enable a detail mode matched with the horizontal position or the vertical position based on the position information of the thumb transmitted from the thumb sensor 200 in the state in which the hand motion mode is enabled after setting of a hand motion to be performed is completed using the fingers of the myoelectric hand.

At this time, of course, the detailed mode of the hand motion mode that is enabled is changed whenever the user manually rotates the thumb to change the position of the thumb from the horizontal position to the vertical position or from the vertical position to the horizontal position.

In addition, the hand motion execution unit 330 is configured to derive a control signal matched with an enabling signal transmitted from the first or second electromyography sensor in the state in which the detail mode selected based on the position of the thumb is enabled and to transmit the control signal to the driving unit of the myoelectric hand.

As shown in FIG. 2, therefore, when the first enabling signal (open signal), in which a value of HIGH is input from only the first electromyography sensor, is applied in the detail mode in which the thumb is located at the vertical position, the hand motion execution unit enables a control signal constituted by driving signals for moving the joints of the fingers so as to show the "thumbs-up" expression matched with the first enabling signal and to transmit the control signal to the driving unit of the myoelectric hand. The fingers of the myoelectric hand are driven according to the control signal transmitted under control of the hand motion execution unit, whereby it is possible to show the "thumbs-up" expression, as shown in FIG. 2.

Afterwards, when a signal (close signal in FIG. 2) opposite the first enabling signal (open signal) is input from the first or second electromyography sensor, the fingers of the myoelectric hand are restored to the state before the hand motion is performed so as to be in a ready state for motion mode switching, detail mode switching, or execution of another hand motion.

In addition, when the second enabling signal (close signal), in which a value of HIGH is input from only the second electromyography sensor, is applied in the detail mode in which the thumb is located at the vertical position, the hand motion execution unit enables a control signal for moving the joints of the fingers so as to show "indexing" expression matched with the second enabling signal and to transmit the control signal to the driving unit of the myoelectric hand. As a result, the fingers of the myoelectric hand are driven, whereby it is possible to show "indexing" expression indicating an object or a direction, as shown in FIG. 2.

Afterwards, when a signal (open signal in FIG. 2) opposite the second enabling signal (close signal) is input from the first or second electromyography sensor, the fingers of the myoelectric hand are restored to the state before the hand motion is performed.

In addition, as shown in FIG. 2, when the first enabling signal (open signal), in which a value of HIGH is input from only the first electromyography sensor, is applied in the detail mode in which the thumb is located at the horizontal position, the hand motion execution unit enables a control signal for moving the joints of the fingers so as to show the "victory" expression matched with the first enabling signal and to transmit the control signal to the driving unit of the myoelectric hand. As a result, the fingers of the myoelectric hand are driven, whereby it is possible to show the "victory" expression, as shown in FIG. 2.

Afterwards, when a signal (close signal in FIG. 2) opposite the first enabling signal (open signal) is input from the first or second electromyography sensor, the fingers of the myoelectric hand are restored to the state before the hand motion is performed.

In addition, when the second enabling signal (close signal), in which a value of HIGH is input from only the second electromyography sensor, is applied in the detail mode in which the thumb is located at the horizontal position, the hand motion execution unit enables a control signal for moving the joints of the fingers so as to show the "OK" expression matched with the second enabling signal and to transmit the control signal to the driving unit of the myoelectric hand. As a result, the fingers of the myoelectric hand are driven, whereby it is possible to show the "OK" expression, as shown in FIG. 2.

Afterwards, when a signal (open signal in FIG. 2) opposite the second enabling signal (close signal) is input from the first or second electromyography sensor, the fingers of the myoelectric hand are restored to the state before the hand motion is performed.

In addition, the grasping motion controller 400 includes a grasping motion setting unit 410 configured to store a control signal matched with a driving signal for manipulating the driving unit of the myoelectric hand so as to grasp an object while unbending or bending fingers according to an enabling signal constituted by an electromyography signal transmitted from the first or second electromyography sensor in each detail mode of the grasping motion mode, a thumb sensing unit 420 configured to select and enable a detail mode matched with position information of the thumb transmitted from the thumb sensor in the state in which the grasping motion mode is enabled, and a grasping motion execution unit 430 configured to derive a preset control signal according to an enabling signal transmitted from the first or second electromyography sensor in the state in which the detail mode selected by the thumb sensing unit is enabled and to transmit the control signal to the driving unit.

As described above, the grasping motion controller 400 is also configured to store control signals pre-matched with driving signals for unbending or bending fingers according to the first or second enabling signals in each detail mode, in the same manner as in the hand mode controller 300, whereby it is possible for the user to perform both the hand motion and the grasping motion using the same enabling signal transmitted from the first or second electromyography sensor.

To this end, the grasping motion setting unit 410 is configured to generate and store a control signal in which each enabling signal is matched with a driving signal for bending or unbending the joints of the fingers in order to show a first grasping motion to be performed in a first enabling signal state in which a value of HIGH is input from the first electromyography sensor and a value of LOW is input from the second electromyography sensor and a second grasping motion to be performed in a second enabling signal state in which a value of LOW is input from the first electromyography sensor and a value of HIGH is input from the second electromyography sensor in a detail mode in which the thumb is located at the vertical position.

In addition, the grasping motion setting unit 410 is also configured to generate and store a control signal in which each enabling signal is matched with a driving signal for bending or unbending the joints of the fingers in order to show a third grasping motion to be performed in the first enabling signal state and a fourth grasping motion to be performed in the second enabling signal state in a detail mode in which the thumb is located at the horizontal position.

In this embodiment, as shown in FIG. 2, in the detail mode in which the thumb is located at the vertical position, a grip for covering an object having a round outer circumferential surface, such as a cylinder or a rod, (expressed as a "cylinder" grip in FIG. 2) and a grip for stably holding one surface of a thin and wide object, such as a card, (expressed as a "lateral" grip in FIG. 2) are set. Also, in the detail mode in which the thumb is located at the horizontal position, a grip for widely covering the outer circumferential surface of a large object (expressed as a "power" grip in FIG. 2) and a grip for lightly holding a small object using some fingers (expressed as a "tip (precision)" grip in FIG. 2) are set. However, the type of the grip set in each detail mode is not limited thereto and may be variously set depending on the form of the grip mainly used by the user.

At this time, it is preferable for the grasping motion setting unit 410 to set a finger grip process of covering an object and a releasing process so as to be sequentially and stepwise performed when an enabling signal from the first or second electromyography sensor is changed so as to stably wrap the outer circumferential surface of the object in a process of grasping the object.

As a result, in this embodiment, as shown in FIG. 2, in the "cylinder" grip, grasping is completed when the first enabling signal (open signal) and the second enabling signal (close signal) are sequentially input, and restoring is completed when the first enabling signal (open signal) and the second enabling signal (close signal) are sequentially input again.

Also, in the "power" grip, grasping is completed when the first enabling signal (open signal) and the second enabling signal (close signal) are sequentially input, and restoring is completed when the first enabling signal (open signal) is input again.

Since completion of grasping and restoring is not achieved by a single enabling signal but by a combination of enabling signals that are sequentially input, as described above, more stable and stepwise grasping is possible.

In addition, the thumb sensing unit 420 is configured to enable a detail mode matched with the horizontal position or the vertical position based on the position information of the thumb transmitted from the thumb sensor in the state in which the grasping motion mode is enabled, in the same manner as in the hand motion controller 300.

In addition, the grasping motion execution unit 430 is configured to derive a control signal matched with an enabling signal transmitted from the first or second electromyography sensor in the state in which the detail mode selected based on the position of the thumb is enabled and to transmit the control signal to the driving unit of the myoelectric hand.

As shown in FIG. 2, therefore, when the first enabling signal (open signal), in which a value of HIGH is input from only the first electromyography sensor, is applied in the detail mode in which the thumb is located at the vertical position, the grasping motion execution unit is converted into a state in which the fingers are unbent in order to form the "cylinder" grip, and when the second enabling signal (close signal), in which a value of HIGH is input from only the second electromyography sensor, is applied, distal ends of the fingers except for the thumb are curled to cover an object having a round outer circumferential surface, such as a rod or a cylinder. Afterwards, when the first enabling signal (open signal), in which a value of HIGH is input from only the first electromyography sensor, is applied, the fingers are unbent again and are then restored to the state before grasping is performed.

In addition, when the second enabling signal (close signal), in which a value of HIGH is input from only the second electromyography sensor, is applied first in the detail mode in which the thumb is located at the vertical position, the grasping motion execution unit forms the "lateral" grip to stably grasp a wide surface of a thin object, such as a card. Afterwards, when the first enabling signal (open signal), in which a value of HIGH is input from only the first electromyography sensor, is applied, the fingers are restored to the state before grasping is performed.

In addition, when the first enabling signal (open signal), in which a value of HIGH is input from only the first electromyography sensor, is applied in the detail mode in which the thumb is located at the horizontal position, the grasping motion execution unit is converted into a state in which the fingers are unbent in order to form the "power" grip, and when the second enabling signal (close signal), in which a value of HIGH is input from only the second electromyography sensor, is applied, distal ends of all of the thumb and the fingers are curled to more strongly cover an object. Afterwards, when the first enabling signal (open signal), in which a value of HIGH is input from only the first electromyography sensor, is applied, the thumb and the fingers are restored to the state before grasping is performed.

In addition, when the second enabling signal (close signal), in which a value of HIGH is input from only the second electromyography sensor, is applied first in the detail mode in which the thumb is located at the horizontal position, the grasping motion execution unit forms the "tip (precision)" grip to lightly grasp a small object using only the thumb and the index finger. Afterwards, when the first enabling signal (open signal), in which a value of HIGH is input from only the first electromyography sensor, is applied, the thumb and the index finger are restored to the state before grasping is performed.

In the thumb-based hand motion control system of the myoelectric hand according to the present invention, as described above, a hand motion used to express user emotion or intention is set as a mode different from a grasping motion for picking up an object, and data set for a motion in any one mode are configured not to affect a motion in another mode, whereby it is possible to perform a simple hand motion as well as a grasping motion driven in various detail modes using only an enabling signal constituted by electromyography signals transmitted from the two electromyography sensors without assistance of an additional device, such as another application (APP) or dongle, and therefore it is possible to conveniently expand the range in which the myoelectric hand is used.

Also, in the present invention, a manipulation method that the user must learn in order to perform the grasping motion is applicable without change after the motion mode is changed to the hand motion mode, whereby it is possible to minimize inconvenience in learning a complicated and difficult manipulation method.

Next, a thumb-based hand motion control method of the myoelectric hand according to the present invention constructed as described above will be described.

Figure 3:
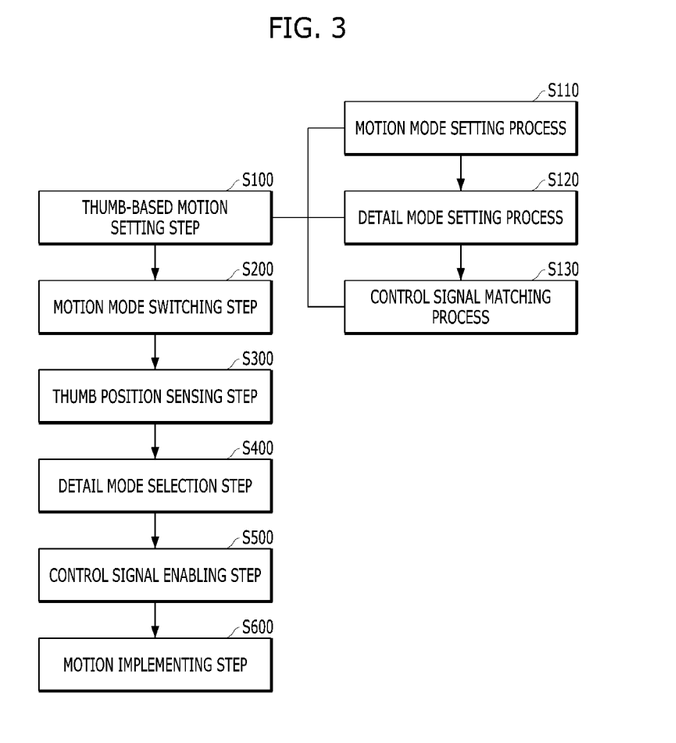
FIG. 3 is a flowchart of a thumb-based hand motion control method of a myoelectric hand showing hand motions and grasping motions in accordance with the present invention.

Referring to FIG. 3, the thumb-based hand motion control method of the myoelectric hand according to the present invention includes a thumb-based motion setting step (S100) of classifying motion modes to be implemented by the myoelectric hand into a hand motion mode and a grasping motion mode and setting and storing, for each motion mode, a control signal for forming the shape of fingers or a grip to be implemented in each motion mode, a motion mode switching step (S200) of, when HIGH signals are input from two electromyography sensors provided at the myoelectric hand, switching a motion mode to be enabled between the hand motion mode and the grasping motion mode, a thumb position sensing step (S300) of acquiring the position of a thumb manipulated by a user based on position information transmitted from a thumb sensor, a detail mode selection step (S400) of determining whether the position of the thumb is a horizontal position or a vertical position and enabling a detail mode set in each motion mode, a control signal enabling step (S500) of deriving a control signal for performing a hand motion or a grasping motion set in each detail mode according to electromyography signals transmitted from the two electromyography sensors, and a motion implementing step (S600) of, upon receiving the enabled control signal, the myoelectric hand performing the set hand motion or grasping motion while bending or unbending the joints of the fingers.

The thumb-based motion setting step (S100) includes a motion mode setting process (S110) of setting motions to be implemented by the myoelectric hand so as to be classified into a hand motion mode for showing the shapes of fingers used for emotion expression or intention expression and a grasping motion mode for forming various grips to hold an object, a detail mode setting process (S120) of storing the shapes of fingers or grips to be implemented in each motion mode in a state of being matched with the vertical position and the horizontal position based on position information of the thumb, and a control signal matching process (S130) of storing a control signal for driving the myoelectric hand such that the joints of the fingers are bent or unbent in order to implement the shapes of fingers and the grips matched respectively with the vertical position and the horizontal position of the thumb in the detail mode in a state of being matched with each shape of fingers and each grip.

In the thumb-based motion setting step (S100), as described above, both the hand motion and the grasping motion are implemented according to restrictive electromyography signals transmitted from the two electromyography sensors, and the detail mode is set based on the position of the thumb that can be changed by the user manually rotating the thumb in order to diversify hand motions and grips that can be implemented.

In the hand motion mode, therefore, it is possible to perform a plurality of hand motions through a detail mode changed depending on the position of the thumb even though the electromyography signals transmitted from the two electromyography sensors are the same. In the same manner, even in the grasping motion mode, a grasping grip different for each detail mode changed depending on the position of the thumb is implemented using the same electromyography signals.

In the motion mode switching step (S200), whenever a simultaneous enabling signal (co-contraction signal) constituted by electromyography signals each having a value of HIGH is input from the two electromyography sensors provided at the myoelectric hand, a motion mode to be enabled is switched between the hand motion mode and the grasping motion mode.

Consequently, it is possible for the user to perform manipulation such that a value of HIGH is input from each of the two electromyography sensors in the same manner as a method learned for an ordinary grasping motion without manipulation of an application (APP) or dongle installed in a separate smartphone, whereby it is possible to switch between the hand motion mode and the grasping motion mode.

In the thumb position sensing step (S300), the position of the thumb manually rotated by the user is acquired based on the position information transmitted from the thumb sensor, and a determination is made as to whether the thumb is at the vertical position, at which the thumb is perpendicular to the fingers, or the thumb is rotated and is at the horizontal position, at which the thumb is parallel to the fingers.

In the detail mode selection step (S400), the detail mode matched with the horizontal position or the vertical position based on the position of the thumb determined in the thumb position sensing step is selected as a detail mode of the hand motion mode or the grasping motion mode to be enabled according to the electromyography signal transmitted from the electromyography sensor.

Consequently, whenever the position of the thumb is changed within the motion mode selected by the user in the motion mode switching step (S200), a detail mode showing the hand motion to be enabled according to the electromyography signal or showing a grip for grasping an object is changed, whereby it is possible to maintain diversity in hand motions and grasping grips that can be performed using the myoelectric hand while using a simultaneous enabling signal in order to switch the motion mode.

In the control signal enabling step (S500), a control signal set to form the shape of fingers and the grasping grip set in each detail mode selected in the detail mode selection step according to the electromyography signals transmitted from the two electromyography sensors is derived.

At this time, driving signals for driving the driving unit provided at the myoelectric hand in order to bend or unbend the joints of several fingers of the myoelectric hand so as to implement the shape of fingers and the grip to be formed are matched with the control signal. It is possible to enable driving signals for forming the shape of fingers and the grasping grip merely by deriving a control signal based on the two electromyography signals input through the two electromyography sensors.

In the motion implementing step (S600), a driving signal matched with the control signal enabled in the control signal enabling step is transmitted to the driving unit of the myoelectric hand such that a preset shape of the fingers or a preset grasping grip is formed.

As described above, it is possible to perform an ordinary grasping motion using the same electromyography signals transmitted from the two electromyography sensors and to perform a hand motion for showing simple intention expression or emotion expression without a separate additional device, whereby it is possible to improve daily convenience and quality of life of the user who wears the myoelectric hand.

While the technical idea of the present invention has been described with reference to the accompanying drawings, this illustratively describes preferred embodiments of the present invention, not restricts the present invention. In addition, a person having ordinary skill in the art to which the present invention pertains will appreciate that various modifications and alterations are possible without departing from the category of the technical idea of the present invention.

The invention claimed is:

1. A thumb-based hand motion control system of a myoelectric hand, the thumb-based hand motion control system comprising:
   a motion mode switching unit configured to switch a motion that is performed by the myoelectric hand between a hand motion mode for intention and emotion expression and a grasping motion mode for holding an object to change a controller to be enabled;
   a thumb sensor configured to determine whether a thumb provided at the myoelectric hand is located at a horizontal position or a vertical position;
   a hand motion controller configured to, when a detail mode matched with each of the horizontal position and the vertical position depending on a position of the thumb is selected in the hand motion mode enabled by the motion mode switching unit, receive an electromyography signal transmitted from at least one of first and second electromyography sensors attached to a human body, to enable a control signal for driving the myoelectric hand in order to implement a hand motion matched with each detail mode, and to transmit the control signal to a driving unit of the myoelectric hand; and a grasping motion controller configured to, when a detail mode matched with each of the horizontal position and the vertical position depending on the position of the thumb is selected in the grasping motion mode enabled by the motion mode switching unit, receive an electromyography signal transmitted from at least one of the first and second electromyography sensors, to enable a control signal for driving the myoelectric hand in order to implement a grasping motion matched with each detail mode, and to transmit the control signal to the driving unit of the myoelectric hand.

2. The thumb-based hand motion control system according to claim 1, wherein the motion mode switching unit switches the controller to be enabled between the hand motion controller and the grasping motion controller whenever a simultaneous enabling signal, in which values of HIGH are applied from both the first and second electromyography sensors, is input.

3. The thumb-based hand motion control system according to claim 2, wherein the hand motion controller comprises:
a hand motion setting unit configured to store a control signal matched with a driving signal for manipulating the driving unit of the myoelectric hand so as to unbend or bend fingers according to an enabling signal constituted by the electromyography signal transmitted from the first or second electromyography sensor in each detail mode of the hand motion mode;
a thumb sensing unit configured to select and enable a detail mode matched with position information of the thumb transmitted from the thumb sensor in a state in which the hand motion mode is enabled; and
a hand motion execution unit configured to derive a preset control signal according to the enabling signal transmitted from the first or second electromyography sensor in a state in which the detail mode selected by the thumb sensing unit is enabled and to transmit the control signal to the driving unit.

4. The thumb-based hand motion control system according to claim 3, wherein the hand motion setting unit is configured to generate and store a control signal in which each enabling signal is matched with a driving signal for bending or unbending joints of the fingers in order to show a first hand motion to be performed in a first enabling signal state in which a value of HIGH is input from the first electromyography sensor and a value of LOW is input from the second electromyography sensor and a second hand motion to be performed in a second enabling signal state in which a value of LOW is input from the first electromyography sensor and a value of HIGH is input from the second electromyography sensor in a detail mode of the hand motion mode in which the thumb is located at the vertical position.

5. The thumb-based hand motion control system according to claim 4, wherein the hand motion setting unit performs setting:
such that the first enabling signal state indicates a "thumbs-up" hand motion and the second enabling signal state indicates an "indexing" hand motion in the detail mode in which the thumb is located at the vertical position; and
such that the first enabling signal state expresses a hand motion corresponding to "V" indicating "victory" and the second enabling signal state expresses a hand motion indicating "OK" in the detail mode in which the thumb is located at the horizontal position.

6. The thumb-based hand motion control system according to claim 3, wherein the hand motion setting unit is configured to generate and store a control signal in which each enabling signal is matched with a driving signal for bending or unbending joints of the fingers in order to show a third hand motion to be performed in a first enabling signal state in which a value of HIGH is input from the first electromyography sensor and a value of LOW is input from the second electromyography sensor and a fourth hand motion to be performed in a second enabling signal state in which a value of LOW is input from the first electromyography sensor and a value of HIGH is input from the second electromyography sensor in a detail mode of the hand motion mode in which the thumb is located at the horizontal position.

7. The thumb-based hand motion control system according to claim 6, wherein the hand motion setting unit performs setting:
such that the first enabling signal state indicates a "thumbs-up" hand motion and the second enabling signal state indicates an "indexing" hand motion in the detail mode in which the thumb is located at the vertical position; and
such that the first enabling signal state expresses a hand motion corresponding to "V" indicating "victory" and the second enabling signal state expresses a hand motion indicating "OK" in the detail mode in which the thumb is located at the horizontal position.

8. The thumb-based hand motion control system according to claim 2, wherein the grasping motion controller comprises:
a grasping motion setting unit configured to store a control signal matched with a driving signal for manipulating the driving unit of the myoelectric hand so as to grasp an object while unbending or bending fingers according to an enabling signal constituted by the electromyography signal transmitted from the first or second electromyography sensor in each detail mode of the grasping motion mode;
a thumb sensing unit configured to select and enable a detail mode matched with position information of the thumb transmitted from the thumb sensor in a state in which the grasping motion mode is enabled; and
a grasping motion execution unit configured to derive a preset control signal according to an enabling signal transmitted from the first or second electromyography sensor in a state in which the detail mode selected by the thumb sensing unit is enabled and to transmit the control signal to the driving unit.

9. The thumb-based hand motion control system according to claim 8, wherein the grasping motion setting unit is configured:
to generate and store a control signal in which each enabling signal is matched with a driving signal for bending or unbending joints of the fingers in order to show a first grasping motion to be performed in a first enabling signal state in which a value of HIGH is input from the first electromyography sensor and a value of LOW is input from the second electromyography sensor and a second grasping motion to be performed in a second enabling signal state in which a value of LOW is input from the first electromyography sensor and a value of HIGH is input from the second electromyography sensor in a detail mode of the grasping motion mode in which the thumb is located at the vertical position; and to generate and store a control signal in which each enabling signal is matched with a driving signal for bending or unbending the joints of the fingers in order to show a third grasping motion to be performed in the first enabling signal state and a fourth grasping motion to be performed in the second enabling signal state in a detail mode of the grasping motion mode in which the thumb is located at the horizontal position.

10. The thumb-based hand motion control system according to claim 9, wherein the grasping motion setting unit performs setting:

such that a cylinder grip is taken in the first enabling signal state and a lateral grip is taken in the second enabling signal state in the detail mode in which the thumb is located at the vertical position; and such that a power grip is taken in the first enabling signal state and a tip (precision) grip is taken in the second enabling signal state in the detail mode in which the thumb is located at the horizontal position.

11. A thumb-based hand motion control method of a myoelectric hand, the thumb-based hand motion control method comprising:

a thumb-based motion setting step of classifying motion modes to be implemented by the myoelectric hand into a hand motion mode and a grasping motion mode and setting and storing, for each motion mode, a control signal for forming a shape of fingers or a grip to be implemented in each motion mode;

a motion mode switching step of, when HIGH signals are input from two electromyography sensors provided at the myoelectric hand, switching a motion mode to be enabled between the hand motion mode and the grasping motion mode;

a thumb position sensing step of acquiring a position of a thumb manipulated by a user based on position information transmitted from a thumb sensor;

a detail mode selection step of determining whether the position of the thumb is a horizontal position or a vertical position and enabling a detail mode set in each motion mode;

a control signal enabling step of deriving a control signal for performing a hand motion or a grasping motion set in each detail mode according to electromyography signals transmitted from the two electromyography sensors; and a motion implementing step of, upon receiving the enabled control signal, the myoelectric hand performing the set hand motion or grasping motion while bending or unbending joints of the fingers.

12. The thumb-based hand motion control method according to claim 11, wherein the thumb-based motion setting step comprises:

a motion mode setting process of setting motions to be implemented by the myoelectric hand so as to be classified into a hand motion mode for showing shapes of fingers used for emotion expression or intention expression and a grasping motion mode for forming various grips to hold an object;

a detail mode setting process of storing the shapes of fingers or grips to be implemented in each motion mode in a state of being matched with the vertical position and the horizontal position based on position information of the thumb; and a control signal matching process of storing a control signal for driving the myoelectric hand such that joints of the fingers of the myoelectric hand are bent or unbent in order to implement the shapes of fingers and the grips matched respectively with the vertical position and the horizontal position of the thumb in the detail mode in a state of being matched with each shape of fingers and each grip.

* * * * *